(12) United States Patent
Yamakawa et al.

(10) Patent No.: US 7,981,318 B2
(45) Date of Patent: Jul. 19, 2011

(54) REACTION REAGENT FOR TRIFLUOROMETHYLATION

(75) Inventors: Tetsu Yamakawa, Nishitokyo (JP); Kyoko Yamamoto, Yokohama (JP); Daisuke Uraguchi, Nagoya (JP); Kenji Tokuhisa, Shunan (JP)

(73) Assignees: Sagami Chemical Research Center, Kanagawa (JP); Tosoh F-Tech, Inc., Yamaguchi (JP)

( * ) Notice: Subject to any disclaimer, the term of this patent is extended or adjusted under 35 U.S.C. 154(b) by 400 days.

(21) Appl. No.: 12/225,249

(22) PCT Filed: Nov. 6, 2007

(86) PCT No.: PCT/JP2007/071575
§ 371 (c)(1),
(2), (4) Date: Sep. 17, 2008

(87) PCT Pub. No.: WO2008/056677
PCT Pub. Date: May 15, 2008

(65) Prior Publication Data
US 2010/0230633 A1 Sep. 16, 2010

(30) Foreign Application Priority Data
Nov. 6, 2006 (JP) ................................. 2006-300571

(51) Int. Cl.
C09K 3/00 (2006.01)
C01B 15/00 (2006.01)
C01B 15/01 (2006.01)

(52) U.S. Cl. ........... 252/182.16; 252/182.12; 252/182.3; 252/182.15; 252/183.11; 252/183.13; 252/186.42; 252/186.43

(58) Field of Classification Search .............. 252/182.12, 252/182.3, 182.15, 182.16, 183.11, 183.13
See application file for complete search history.

(56) References Cited

U.S. PATENT DOCUMENTS

| | | | | |
|---|---|---|---|---|
| 3,226,449 A | * | 12/1965 | Blanchard et al. | 570/139 |
| 3,271,441 A | | 9/1966 | Brace | |
| 4,731,450 A | * | 3/1988 | Wakselman et al. | 546/303 |
| 6,464,895 B2 | * | 10/2002 | Forat et al. | 252/182.12 |
| 2003/0060471 A1 | * | 3/2003 | Okui et al. | 514/252.03 |
| 2004/0230079 A1 | * | 11/2004 | Prakash et al. | 568/56 |
| 2005/0153992 A1 | * | 7/2005 | Tsutsumi et al. | 514/265.1 |
| 2006/0217433 A1 | * | 9/2006 | Conner et al. | 514/418 |
| 2007/0072906 A1 | * | 3/2007 | Giblin et al. | 514/326 |
| 2009/0124796 A1 | * | 5/2009 | Yamakawa et al. | 536/27.6 |

FOREIGN PATENT DOCUMENTS

| | | |
|---|---|---|
| EP | 1 947 092 A1 | 7/2008 |
| WO | WO 2005/054191 A1 | 6/2005 |
| WO | 2007/055170 | 5/2007 |

OTHER PUBLICATIONS

Supplementary European Search Report in EP 07 83 1307 mailed Feb. 22, 2010.
International Search Report for PCT/JP2007/071575 mailed Jan. 22, 2008.
Khanna et al., "1,2-Diarylpyrroles as Potent and Selective Inhibitors of Cyclooxygenase-2", *American Chemical Society*, 40(11), 1997, pp. 1619-1633.
Hall et al., "Structure-activity relationships of 1,5-biaryl pyrroles as $EP_1$ receptor antagonists", *Bioorg. Med. Chem. Lett.*, 16(14), 2006, pp. 3657-3662.
Umemoto et al., "Power-Variable Trifluoromethylating Agents, (Trifluoromethyl)Dibenzothio- and Selenophenium Salt System", *Tetrahedron Letters*, vol. 31, 1990, pp. 3579-3582.
Umemoto et al., "Power-Variable Electrophilic Trifluoromethylating Agents, S-, Se-, and Te-(Trifluoromethyl)Dibenzothio- and -seleno-, and -tellurophenium Salt System", *American Chemical Society*, vol. 115, 1993, pp. 2156-2164.
Umemoto et al, "New Method for Trifluoromethylation of Enolate Anions and Applications to Regio-, Diastereo- and Enantioselective Trifluoromethylation", *Organic Chemistry*, vol. 59, 1994, pp. 5692-5699.
Umemoto et al., "Useful electrophilic trifluoromethylating agents; S-, Se- and Te-(trifluoromethyl)dibenzo-thio-, -seleno- and -tellurophenium-3-sulfonates", *Fluorine Chemistry*, vol. 74, 1995, pp. 77-82.
Ma et al., "Mild Electrophilic Trifluoromethylation of B-Ketoesters and Silyl Enol Ethers with 5-Trifluoro Methyldibenzothiophenium Tetrafluoroborate", *Organic Chemistry*, vol. 68, 2003, pp. 8726-8729.
*Journal of the American Chemical Society*, vol. 107, 1985, pp. 5014-5015.
*Journal of the American Chemical Society*, vol. 108, 1986, pp. 832-834.
Umemoto, "FITS Reagents and New Perfluoroalkylations", *Synthetic Organic Chemistry*, vol. 41, 1983, pp. 251-265.
*Journal of Organic Chemistry*, vol. 53, 1988, pp. 4582-4585.
Kobayashi et al., "Studies on Organic Fluorine Compounds . . . ", *Chemical Society*, Perkin Transaction I, 1980, pp. 2755-2761.
Itoh et al., "Facile Radical Trifluoromethylation of Lithium Enolates", *Organic Letters*, vol. 7, 2005, pp. 4883-4885.
Tordeux et al., "Reactions of Trifluoromethyl Bromide and Related Halides:", *Chemical Society*, Perkin Transaction I, 1990, pp. 2293-2299.
Nowak, et al., "Unusual reaction of sulphur tetrafluoride"., *Fluorine Chemistry*, vol. 75, 1995, pp. 115-116.
Bravo et al., "New Methods of Free Radical Perfluoroalkylation of Aromatics and Alkenes.", *Organic Chemistry*, vol. 62, 1997, pp. 7128-7136.
Baciocchi et al., "Synthesis of Perfluoroalkylpyrroles by Homolytic Substitution with Perfluoroalkyl Radicals", *Tetrahedron Letters*, vol. 34, No. 23, 1993, pp. 3799-3800.

* cited by examiner

*Primary Examiner* — Joseph D Anthony
(74) *Attorney, Agent, or Firm* — Nixon & Vanderhye P.C.

(57) ABSTRACT

Provided is a reaction reagent for trifluoromethylation with high general versatility and good efficiency.
The reaction reagent for trifluoromethylation contains an iron compound, trifluoromethyl iodide, a sulfoxide and a peroxide, and may further contain an acid. The iron compound is, for example, iron(II) sulfate, ammonium iron(II) sulfate, iron (II) tetrafluoroborate, ferrocene, bis($\eta^5$-pentamethylcyclopentadienyl)iron or an iron powder; the sulfoxide is, for example, dimethyl sulfoxide; the peroxide is, for example, hydrogen peroxide or hydrogen peroxide-urea composite; and the acid is, for example, sulfuric acid, tetrafluoroboric acid or trifluoromethanesulfonic acid.

13 Claims, No Drawings

REACTION REAGENT FOR TRIFLUOROMETHYLATION

This application is the U.S. national phase of International Application No. PCT/JP2007/071575 filed 6 Nov. 2007 which designated the U.S. and claims priority to Japanese Patent Application No. 2006-300571 filed 6 Nov. 2006, the entire contents of each of which are hereby incorporated by reference.

TECHNICAL FIELD

The present invention relates to a reaction reagent used for trifluoromethylation.

BACKGROUND ART

It is well known that introduction of a trifluoromethyl group into various organic compounds brings many efficiencies such as improvement in physiological activities of medical and agricultural chemicals and improvement in performance of functional materials. Therefore, reaction reagents for direct trifluoromethylation of an organic compound have been studied heretofore.

Although S-(trifluoromethyl)dibenzothiophenium trifluoromethanesulfonate described in Non-patent Documents 1 to 5 is capable of converting a carbon-hydrogen bond in various organic compounds to a carbon-trifluoromethyl bond, defects thereof are that production of S-(trifluoromethyl)dibenzothiophenium trifluoromethanesulfonate is extremely complicated and is rather expensive.

Although non-patent Documents 6 and 7 disclose trifluoromethylation using dichlorodifluoromethane, dibromodifluoromethane or bromochlorodifluoromethane, and cadmium, zinc or copper, application thereof is restricted to a substitution reaction of a halogen in an organic halide with a trifluoromethyl group.

Non-patent Document 8 describes that benzenes are converted to the corresponding trifluoromethylbenzenes with use of (trifluoromethyl)phenyliodonium trifluoromethanesulfonate obtained by oxidizing trifluoromethyl iodide with hydrogen peroxide in trifluoroacetic anhydride and then reacting the resultant with trifluoromethanesulfonic acid and benzene. However, production of (trifluoromethyl)phenyliodonium trifluoromethanesulfonate is complicated and is industrially hard to employ.

Non-patent Document 9 discloses trifluoromethylation of nucleobases and benzenes using trifluoroacetic acid and xenon difluoride. However, xenon difluoride is not suitable for use in an industrial scale because xenon, which is a starting material of xenon difluoride, is expensive and xenon difluoride is unstable to water.

Non-patent Document 10 discloses a method using copper powder and trifluoromethyl iodide, as a process for direct trifluoromethylation of an organic compound with trifluoromethyl halide. However, this process has problems that it uses hexamethylphosphoric triamide, which is industrially hard to handle, as a solvent and that it uses a copper compound which imposes a heavy burden on the environment. Although another known method is that using trifluoromethyl iodide and triethylborane (Non-patent Document 11), an applicable substrate is restricted to a carbonyl compound which can undergo enolization with lithium diisopropyl amide. Moreover, Non-patent Document 12 discloses that benzenes, pyridines and pyrroles can be trifluoromethylated by the use of trifluoromethyl bromide, zinc and sulfur dioxide. This document also describes that the same reaction proceeds by the use of trifluoromethyl bromide and sodium dithionite. Because both methods use the toxic substance containing sulfur, they are industrially hard to use.

Patent Document 1 discloses perfluoroalkylation of benzenes using perfluoroalkyl iodide and di-tert-butyl peroxide. Di-tert-butyl peroxide used in this method is highly explosive and industrially hard to employ.

Non-patent Document 13 discloses a method of converting a carboxyl group on a furan ring to a trifluoromethyl group with sulfur tetrafluoride. However, the method has problems that an applicable substrate is restricted to that having a carboxyl group, and that toxic sulfur tetrafluoride is used.

On the other hand, although perfluorobutylation of benzenes with perfluorobutyl iodide in dimethyl sulfoxide in the presence of iron(II) sulfate and hydrogen peroxide (Non-patent Document 14) and perfluoropropylation and perfluorobutylation of pyrroles and indoles with perfluoropropyl iodide or perfluorobutyl iodide in dimethyl sulfoxide in the presence of iron(II) sulfate and hydrogen peroxide (Non-patent Document 15) are known, there is no reaction example using trifluoromethyl iodide and no description on a reaction reagent for trifluoromethylation according to the present invention.

Non-patent Document 1: Tetrahedron Letters, Vol. 31, pp. 3579-3582, 1990
Non-patent Document 2: Journal of the American Chemical Society, Vol. 115, pp. 2156-2164, 1993
Non-patent Document 3: Journal of Organic Chemistry, Vol. 59, pp. 5692-5699, 1994
Non-patent Document 4: Journal of Fluorine Chemistry, Vol. 74, pp. 77-82, 1995
Non-patent Document 5: Journal of Organic Chemistry, Vol. 68, pp. 8726-8729, 2003
Non-patent Document 6: Journal of the American Chemical Society, Vol. 107, pp. 5014-5015, 1985
Non-patent Document 7: Journal of the American Chemical Society, Vol. 108, pp. 832-834, 1986
Non-patent Document 8: Journal of Synthetic Organic Chemistry, Japan, Vol. 41, pp. 251-265, 1983
Non-patent Document 9: Journal of Organic Chemistry, Vol. 53, pp. 4582-4585, 1988
Non-patent Document 10: Journal of Chemical Society, Perkin Transaction I, pp. 2755-2761, 1980
Non-patent Document 11: Organic Letters, Vol. 7, pp. 4883-4885, 2005
Non-patent Document 12: Journal of Chemical Society, Perkin Transaction I, pp. 2293-2299, 1990
Non-patent Document 13: Journal of Fluorine Chemistry, Vol. 75, pp. 115-116, 1995
Patent Document 1: U.S. Pat. No. 3,271,441
Non-patent Document 14: Journal of Organic Chemistry, Vol. 62, pp. 7128-7136, 1997
Non-patent Document 15: Tetrahedron Letters, Vol. 34, pp. 3799-3800, 1993

DISCLOSURE OF THE INVENTION

Object to be Accomplished by the Invention

An object of the present invention is to provide a reaction reagent for trifluoromethylation with high general versatility and good efficiency.

Means to Accomplish the Object

In order to accomplish the above object, the inventors of the present invention have conducted intensive and extensive studies and found that an appropriate sp² carbon was trifluoromethylated by the use of a reaction reagent comprising an iron compound, trifluoromethyl iodide, a peroxide and a sulfoxide so as to accomplish the present invention.

Namely, the present invention has the following aspects:
(1) A reaction reagent for trifluoromethylation comprising an iron compound, trifluoromethyl iodide, a peroxide and a sulfoxide.
(2) The reaction reagent according to the above aspect (1), further comprising an acid.
(3) The reaction reagent according to the above aspect (1) or (2), wherein a molar ratio of the iron compound and trifluoromethyl iodide is in a range of from 1:1 to 1:100.
(4) The reaction reagent according to any one of the above aspects (1) to (3), wherein a molar ratio of the iron compound and the peroxide is in a range of from 1:1 to 1:50.
(5) The reaction reagent according to any one of the above aspects (1) to (4), wherein a molar ratio of the iron compound and the sulfoxide is in a range of from 1:50 to 1:30000.
(6) The reaction reagent according to any one of the above aspects (1) to (5), wherein a molar ratio of the iron compound and the acid is in a range of from 1:0.001 to 1:50.
(7) The reaction reagent according to any one of the above aspects (1) to (6), wherein the iron compound is iron(II) sulfate, ammonium iron(II) sulfate, iron(II) tetrafluoroborate, iron(II) chloride, iron(II) bromide, iron(II) iodide, iron(II) acetate, iron(II) oxalate, bis(acetylacetonato)iron (II), ferrocene, bis($\eta^5$-pentamethylcyclopentadienyl)iron or an iron powder.
(8) The reaction reagent according to any one of the above aspects (1) to (6), wherein the iron compound is iron(II) sulfate, ammonium iron(II) sulfate, iron(II) tetrafluoroborate, ferrocene, bis($\eta^5$-pentamethylcyclopentadienyl)iron or an iron powder.
(9) The reaction reagent according to any one of the above aspects (1) to (8), wherein the peroxide is hydrogen peroxide, hydrogen peroxide-urea composite, tert-butyl peroxide or peroxyacetic acid.
(10) The reaction reagent according to any one of the above aspects (1) to (8), wherein the peroxide is hydrogen peroxide or hydrogen peroxide-urea composite.
(11) The reaction reagent according to any one of the above aspects (1) to (10), wherein the sulfoxide is dimethyl sulfoxide, dibutyl sulfoxide or diphenyl sulfoxide.
(12) The reaction reagent according to any one of the above aspects (1) to (10), wherein the sulfoxide is dimethyl sulfoxide.
(13) The reaction reagent according to any one of the above aspects (2) to (12), wherein the acid is sulfuric acid, hydrochloric acid, hydrobromic acid, hydroiodic acid, nitric acid, phosphoric acid, hexafluorophosphoric acid, tetrafluoroboric acid, formic acid, acetic acid, propionic acid, oxalic acid, p-toluenesulfonic acid, trifluoromethanesulfonic acid or trifluoroacetic acid.
(14) The reaction reagent according to any one of the above aspects (2) to (12), wherein the acid is sulfuric acid, tetrafluoroboric acid or trifluoromethanesulfonic acid.

EFFECT OF THE INVENTION

The present invention provides a reaction reagent for trifluoromethylation with high general versatility and good efficiency.

BEST MODE FOR CARRYING OUT THE INVENTION

The iron compound applicable to the reaction reagent for trifluoromethylation of the present invention (which will also be referred to hereinafter as "the present reaction reagent") is preferably an iron(II) salt, examples thereof include inorganic acid salts such as iron(II) sulfate, ammonium iron(II) sulfate, iron(II) tetrafluoroborate, iron(II) chloride, iron(II) bromide and iron(II) iodide, and organometallic compounds such as iron(II) acetate, iron(II) oxalate, bis(acetylacetonato)iron(II), ferrocene and bis($\eta^5$-pentamethylcyclopentadienyl)iron, and these may be used in combination properly. In addition, an iron powder, an iron(0) compound or an iron(I) salt may be used in combination with an oxidizing reagent such as a peroxide so as to generate an iron(II) salt in the system. On this occasion, the peroxide comprising the reaction reagent of the present invention may also be used as the oxidizing reagent as it is.

The iron compound is preferably iron(II) sulfate, ammonium iron(II) sulfate, iron(II) tetrafluoroborate, ferrocene, bis($\eta^5$-pentamethylcyclopentadienyl)iron or an iron powder in terms of a good yield.

Examples of the peroxides applicable to the present invention include hydrogen peroxide, hydrogen peroxide-urea composite, tert-butyl peroxide, peroxyacetic acid, and so on, and these may be used in combination properly. The peroxide is preferably hydrogen peroxide or hydrogen peroxide-urea composite in terms of a good yield.

Hydrogen peroxide may be used after diluting it with water. On this occasion, although the concentration can be from 3 to 70% by weight, commercially available 35% by weight hydrogen peroxide may be used as it is. It is more preferable to dilute hydrogen peroxide with water to the solution, the percentage by weight of which is from 10 to 30% by weight in terms of a good yield and safety.

Examples of the sulfoxides applicable to the present invention include dimethyl sulfoxide, dibutyl sulfoxide, di-sec-butyl sulfoxide, methylphenyl sulfoxide, (R)-(+)-methyl-p-tolyl sulfoxide, (S)-(−)-methyl-p-tolyl sulfoxide or diphenyl sulfoxide, and so on. The sulfoxide is preferably dimethyl sulfoxide, dibutyl sulfoxide or diphenyl sulfoxide, and more preferably dimethyl sulfoxide, in terms of good yield and low cost.

The molar ratio of the iron compound and trifluoromethyl iodide is preferably from 1:1 to 1:100, and more preferably from 1:1 to 1:30.

The molar ratio of the iron compound and the peroxide is preferably from 1:1 to 1:50, and more preferably from 1:1 to 1:10.

The molar ratio of the iron compound and the sulfoxide is preferably from 1:50 to 1:30000, and more preferably from 1:100 to 1:10000.

The present reaction reagent may further contain an acid. For example, an applicable acid may be any one of inorganic acids such as sulfuric acid, hydrochloric acid, hydrobromic acid, hydroiodic acid, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid, and these may be used in combination properly. The acid is preferably sulfuric acid, tetrafluoroboric acid or trifluoromethanesulfonic acid, and more preferably sulfuric acid, in terms of a good yield.

In addition, an acidic salt of sulfuric acid may also be used. Examples of the acidic salts include tetramethylammonium hydrogen sulfate, tetraethylammonium hydrogen sulfate, tetrabutylammonium hydrogen sulfate, tetraphenylphosphonium hydrogen sulfate, and so on.

If the acid is added, the molar ratio of the iron compound and the acid is preferably from 1:0.001 to 1:50, and more preferably from 1:1 to 1:5.

The present reaction reagent can be used at a temperature optionally selected from the range of from 20 to 100° C. The temperature is preferably from 20 to 70° C. in terms of a good yield.

The present reaction reagent can be used in a solvent in accordance with the solubility of the iron compound, trifluoromethyl iodide, the peroxide and the sulfoxide, and/or the solubility of the acid if used.

Examples of applicable solvents include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent may be one of sulfoxides being liquid at the reaction temperature, namely, dimethyl sulfoxide, dibutyl sulfoxide, and so on. The solvent is preferably water, a sulfoxide, or a solvent mixture of water and a sulfoxide in terms of a good yield. An amount of the solvent to be used is so determined that the concentration of the iron compound becomes preferably from 0.1 to 10 mol/l, and more preferably from 0.5 to 5 mol/l, though it depends on the solubility of the iron compound.

Trifluoromethyl iodide may be used in a gaseous state as it is, without converting it to a solution. On this occasion, it may be used as a gas mixture after diluting it with a gas such as argon, nitrogen, air, helium or oxygen, wherein a molar fraction of trifluoromethyl iodide is from 1 to 100%. In the case where the reaction is carried out in a closed system, trifluoromethyl iodide or the gas mixture thereof may be used as a reaction atmosphere. On this occasion, although the pressure can be one optionally taken in the range of from the atmospheric pressure (0.1 MPa) to 1.0 MPa, the reaction sufficiently proceeds even under the atmospheric pressure. On the other hand, trifluoromethyl iodide or the gas mixture thereof may be introduced by bubbling into a reaction solution in an open system. On this occasion, the introduction rate of trifluoromethyl iodide or the gas mixture thereof may be taken in the range of from 1 to 200 ml/min though it depends on a scale of the reaction, an amount of the catalyst, a temperature of the reaction, and a molar fraction of trifluoromethyl iodide in the gas mixture.

By applying the present reaction reagent, various organic compounds as a substrate can be trifluoromethylated, and among others, compounds having an enamine moiety in their molecules, furans, thiophenes and benzenes can be trifluoromethylated efficiently. Examples of the compounds having an enamine moiety include enamines, N-vinyl lactams, uracils, pseudouracils, thymines, cytosines, adenines, guanines, hypoxanthines, xanthines, pyrazoles, indoles, pyrroles, triazoles, anilines, pyridines, primidines, pyrazines, and so on.

The molar ratio of the iron compound and one of these substrates is preferably from 1:0.1 to 1:1000, and more preferably from 1:1 to 1:50.

There are no particular restrictions on the order of loading the iron compound, trifluoromethyl iodide, the peroxide and the sulfoxide of the reaction reagent of the present invention into contact with the reaction substrate and they may be brought into contact sequentially or all together with the substrate.

EXAMPLES

Now, the present invention will be described in further detail with reference to Examples, but it should be understood that the present invention is by no means restricted to such examples.

Example 1

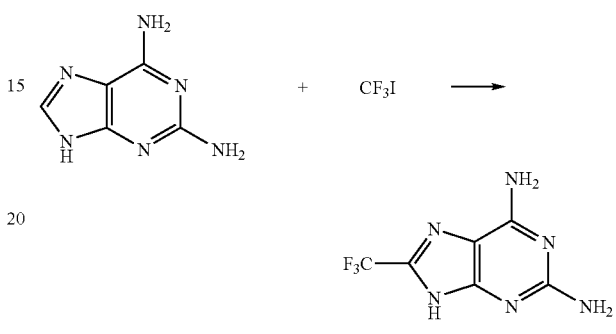

0.12 g (0.8 mmol) of 2,6-diaminopurine was weighed and placed in a two-neck flask and the atmosphere in the flask was replaced with argon. The following materials were added thereinto: 3.0 ml of dimethyl sulfoxide, 0.8 ml of a 3.0 mol/l dimethyl sulfoxide solution of trifluoromethyl iodide, 0.25 ml of a 1.0 mol/l aqueous solution of iron(II) sulfate and 0.15 ml of a 30% hydrogen peroxide aqueous solution, and the mixture was stirred for 20 minutes. During the stirring, the temperature of the reaction system rose up in the range of from 40° C. to 50° C. Thereafter, the resulting solution was cooled to room temperature. Formation of 2,6-diamino-8-trifluoromethylpurine ($^{19}$F-NMR yield: 40%) was confirmed by $^{19}$F-NMR with 2,2,2-trifluoroethanol as an internal standard. Water was added to the resulting solution, sodium hydrogen carbonate was added thereto to neutralize, and the desired product was extracted with ethyl acetate. The extract was passed through column chromatography and concentrated under reduced pressure to obtain 2,6-diamino-8-trifluoromethylpurine as a white solid (0.043 g, yield: 20%).

$^1$H-NMR (deuterated dimethyl sulfoxide): δ6.17 (s, 2H), 7.26 (s, 2H), 12.2 (brs, 1H).

$^{13}$C-NMR (deuterated dimethyl sulfoxide): δ114.8, 116.0 (q, $J_{CF}$=269.1 Hz): 144.3, 152.7, 157.0, 161.7.

$^{19}$F-NMR (deuterated dimethyl sulfoxide): δ−62.6.

MS (m/z): 218 [M]$^+$.

Example 2

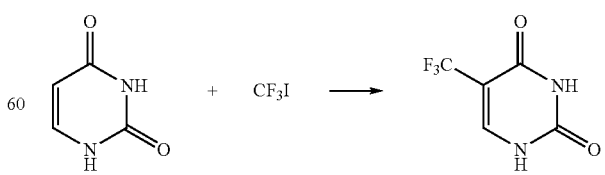

0.055 g (0.5 mmol) of uracil was weighed and placed in a two-neck flask and the atmosphere in the flask was replaced with argon. The following materials were added thereinto: 1.0 ml of a 1 N dimethyl sulfoxide solution of sulfuric acid, 0.5 ml of a 2.1 mol/l dimethyl sulfoxide solution of trifluoromethyl iodide, 0.1 ml of a 30% hydrogen peroxide aqueous solution and 0.15 ml of a 1.0 mol/l aqueous solution of iron(II) sulfate, and the mixture was stirred for 20 minutes. During the stirring, the temperature of the reaction system rose up in the range of from 40° C. to 50° C. Thereafter, the resulting solution was cooled to room temperature. Formation of 5-trifluoromethyluracil ($^{19}$F-NMR yield: 90%) was confirmed by $^{19}$F-NMR with 2,2,2-trifluoroethanol as an internal standard. 5-trifluoromethyluracil was obtained as a white solid (0.16 g, yield: 87%) in the same manner as in Example 1.

$^1$H-NMR (deuterated acetone): δ8.09 (s, 1H), 10.5 (brs, 2H).

$^{13}$C-NMR (deuterated acetone): δ104.0 (q, $J_{CF}$=32.4 Hz), 123.6 (q, $J_{CF}$=268.2 Hz), 144.2 (q, $J_{CF}$=5.9 Hz), 150.9, 160.2.

$^{19}$F-NMR (deuterated acetone): δ−64.1.

MS (m/z): 180 [M]$^+$.

Example 3

Formation of 5-trifluoromethyluracil ($^{19}$F-NMR yield: 75%) was confirmed in the same manner as in Example 2, except that a 1.0 mol/l aqueous solution of ammonium iron (II) sulfate was used instead of the 1.0 mol/l aqueous solution of iron(II) sulfate.

Example 4

0.055 g (0.5 mmol) of uracil and 0.014 g (0.25 mmol) of iron powder were weighed and placed in a two-neck flask and the atmosphere in the flask was replaced with argon. The following materials were added thereto: 1.0 ml of dimethyl sulfoxide, 1.0 ml of a 1 N dimethyl sulfoxide solution of sulfuric acid, 0.5 ml of a 3.0 mol/l dimethyl sulfoxide solution of trifluoromethyl iodide and 0.1 ml of a 30% hydrogen peroxide aqueous solution, and the mixture was stirred for 20 minutes. During the stirring, the temperature of the reaction system rose up in the range of from 40° C. to 50° C. Thereafter, the resulting solution was cooled to room temperature. The subsequent procedure was conducted in the same manner as in Example 2 and formation of 5-trifluoromethyluracil was confirmed ($^{19}$F-NMR yield: 30%).

Example 5

0.055 g (0.5 mmol) of uracil was weighed and placed in a two-neck flask and the atmosphere in the flask was replaced with argon. The following materials were added thereto: 0.1 ml of a 42% aqueous solution of tetrafluoroboric acid, 1.0 ml of dimethyl sulfoxide, 1.5 ml of a 2.0 mol/l dimethyl sulfoxide solution of trifluoromethyl iodide, 0.15 ml of a 1.0 mol/l aqueous solution of iron(II) tetrafluoroborate and 0.1 ml of a 30% hydrogen peroxide aqueous solution, and the mixture was stirred 20 minutes. During the stirring, the temperature of the reaction system rose up in the range of from 40° C. to 50° C. Thereafter, the resulting solution was cooled to room temperature. The subsequent procedure was conducted in the same manner as in Example 2 and formation of 5-trifluoromethyluracil was confirmed ($^{19}$F-NMR yield: 88%).

Example 6

0.055 g (0.5 mmol) of uracil was weighed and placed in a two-neck flask and the atmosphere in the flask was replaced with argon. The following materials were added thereto: 1.0 ml of a 1 N dimethyl sulfoxide solution of sulfuric acid, 1.5 ml of a 2.0 mol/l dimethyl sulfoxide solution of trifluoromethyl iodide, 0.06 g of hydrogen peroxide-urea composite and 0.15 ml of a 1 mol/l aqueous solution of iron(II) sulfate, and the mixture was stirred for 20 minutes. During the stirring, the temperature of the reaction system rose up in the range of from 40° C. to 50° C. Thereafter, the resulting solution was cooled to room temperature. The subsequent procedure was conducted in the same manner as in Example 2 and formation of 5-trifluoromethyluracil was confirmed ($^{19}$F-NMR yield: 66%).

Example 7

Formation of 5-trifluoromethyluracil ($^{19}$F-NMR yield: 36%) was confirmed exactly in the same manner as in Example 2, except that dimethyl sulfoxide was used instead of the 1 N dimethyl sulfoxide solution of sulfuric acid.

Example 8

0.055 g (0.5 mmol) of uracil was weighed and placed in a two-neck flask and the atmosphere in the flask was replaced with trifluoromethyl iodide. The following materials were added thereto: 2.5 ml of dibutyl sulfoxide, 0.027 ml of concentrated sulfuric acid, 0.1 ml of a 30% hydrogen peroxide aqueous solution and 0.15 ml of a 1.0 mol/l aqueous solution of iron(II) sulfate, and the mixture was stirred for 20 minutes. During the stirring, the temperature of the reaction system rose up in the range of from 40° C. to 50° C. Thereafter, the resulting solution was cooled to room temperature. Formation of 5-trifluoromethyluracil ($^{19}$F-NMR yield: 0.19%) was confirmed by $^{19}$F-NMR with 2,2,2-trifluoroethanol as an internal standard.

Example 9

0.055 g (0.5 mmol) of uracil was weighed and placed in a two-neck flask and the atmosphere in the flask was replaced with trifluoromethyl iodide. The following materials were added thereto: 2.5 g of diphenyl sulfoxide, 0.027 ml of concentrated sulfuric acid, 0.1 ml of a 30% hydrogen peroxide aqueous solution and 0.15 ml of a 1.0 mol/l aqueous solution of iron(II) sulfate, and the mixture was stirred for 20 minutes. During the stirring, the temperature of the reaction system rose up in the range of from 40° C. to 50° C. Thereafter, the resulting solution was cooled to room temperature. Formation of 5-trifluoromethyluracil ($^{19}$F-NMR yield: 0.47%) was confirmed by $^{19}$F-NMR with 2,2,2-trifluoroethanol as an internal standard.

Example 10

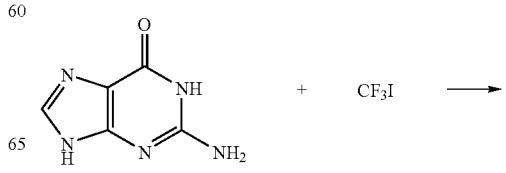

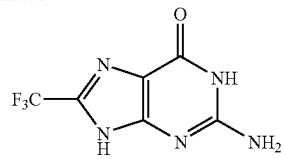

0.10 g (0.67 mmol) of guanine was weighed and placed in a two-neck flask and the atmosphere in the flask was replaced with argon. The following materials were added thereinto: 130 ml of dimethyl sulfoxide, 1.3 ml of a 1 N dimethyl sulfoxide solution of sulfuric acid, 0.7 ml of a 3.0 mol/l dimethyl sulfoxide solution of trifluoromethyl iodide, 0.15 ml of a 30% hydrogen peroxide aqueous solution and 0.2 ml of a 1.0 mol/l aqueous solution of iron(II) sulfate, and the mixture was stirred for 20 minutes. During the stirring, the temperature of the reaction system rose up in the range of from 40° C. to 50° C. Thereafter, the resulting solution was cooled to room temperature. Formation of 8-trifluoromethylguanine ($^{19}$F-NMR yield: 43%) was confirmed by $^{19}$F-NMR with 2,2,2-trifluoroethanol as an internal standard. The subsequent procedure was conducted in the same manner as in Example 1 and 8-trifluoromethylguanine was obtained as a white solid (0.018 g, yield: 8%).

$^1$H-NMR (deuterated dimethyl sulfoxide): δ6.60 (brs, 2H), 10.81 (brs, 1H), 13.73 (brs, 1H).

$^{13}$C-NMR (deuterated dimethyl sulfoxide): δ116.3, 119.2 (q, $J_{CF}$=269.3 Hz), 134.9 (q, $J_{CF}$=40.7 Hz), 152.8, 154.7, 156.6.

$^{19}$F-NMR (deuterated dimethyl sulfoxide): δ−63.0.

MS (m/z): 218 [M-H]$^−$.

Example 11

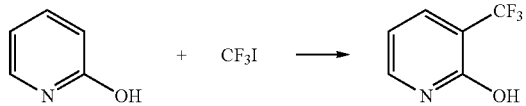

0.19 g (2.0 mmol) of 2-hydroxypyridine and 0.11 g (0.6 mmol) of ferrocene were weighed and placed in a two-neck flask and the atmosphere in the flask was replaced with argon. The following materials were added thereinto: 8.0 ml of dimethyl sulfoxide, 2.0 ml of a 3.0 mol/l dimethyl sulfoxide solution of trifluoromethyl iodide and 0.4 ml of a 30% hydrogen peroxide aqueous solution, and the mixture was stirred for 20 minutes. During the stirring, the temperature of the reaction system rose up in the range of from 40° C. to 50° C. Thereafter, the resulting solution was cooled to room temperature. Formation of 2-hydroxy-3-trifluoromethylpyridine ($^{19}$F-NMR yield: 64%) was confirmed by $^{19}$F-NMR with 2,2,2-trifluoroethanol as an internal standard. The subsequent procedure was conducted in the same manner as in Example 1 and 2-hydroxy-3-trifluoromethylpyridine was obtained as a white solid (0.081 g, yield: 50%).

$^1$H-NMR (deuterated chloroform): δ6.34 (dd, J=6.9, 5.6 Hz, 1H), 7.65 (d, J=5.6 Hz, 1H), 7.88 (d, J=6.9 Hz, 1H), 13.25 (brs, 1H).

$^{13}$C-NMR (deuterated chloroform): δ105.6, 120.4 (q, $J_{CF}$=31.4H z), 122.7 (q, $J_{CF}$=271.3 Hz), 139.2, 140.7 (q, $J_{CF}$=4.9 Hz), 161.4.

$^{19}$F-NMR (deuterated chloroform): δ−66.0.

MS (m/z): 163 [M]$^+$

Example 12

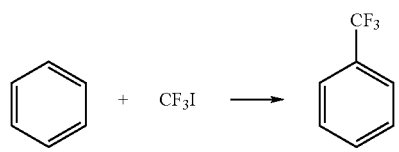

100 µl of benzene, 2.0 ml of dimethyl sulfoxide, 2.0 ml of a 1 N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron(II) sulfate were charged in a two-neck flask in which the atmosphere was replaced with argon, and the mixture was stirred for 20 minutes. During the stirring, the temperature of the reaction system rose up in the range of from 40° C. to 50° C. Thereafter the resulting solution was cooled to room temperature. Formation of trifluoromethylbenzene ($^{19}$F-NMR yield: 20%) was confirmed by $^{19}$F-NMR with 2,2,2-trifluoroethanol as an internal standard. The subsequent procedure was conducted in the same manner as in Example 1 and trifluoromethylbenzene was obtained as a colorless oil (0.02 g, yield: 13%).

$^1$H-NMR (deuterated chloroform): δ7.74 (m, 5H).

$^{13}$C-NMR (deuterated chloroform): δ124.3 (q, $J_{CF}$=266.4 Hz), 125.3 (q, $J_{CF}$=3.0 Hz), 128.8, 130.8 (q, $J_{CF}$=31.5 Hz), 131.8.

$^{19}$F-NMR (deuterated chloroform): δ−63.1.

MS (m/z): 146 [M]$^+$.

Example 13

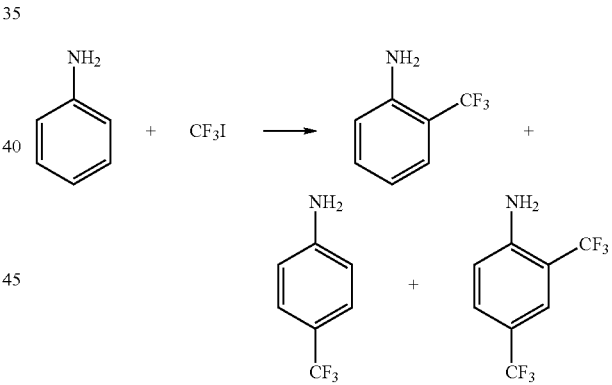

180 µl of aniline, 5.0 ml of dimethyl sulfoxide, 4.0 ml of a 1 N dimethyl sulfoxide solution of sulfuric acid, 0.7 ml of a 3.0 mol/l dimethyl sulfoxide solution of trifluoromethyl iodide, 0.4 ml of a 30% hydrogen peroxide aqueous solution and 0.6 ml of a 1.0 mol/l aqueous solution of iron(II) sulfate were charged in a two-neck flask in which the atmosphere was replaced with argon, and the mixture was stirred for 20 minutes. During the stirring, the temperature of the reaction system rose up in the range of from 40° C. to 50° C. Thereafter, the resulting solution was cooled to room temperature. A molecular weight and a retention time obtained by $^{19}$F-NMR and GC-MS were compared with those of a commercially available standard specimen to confirm formation of each of 2-trifluoromethylaniline ($^{19}$F-NMR yield: 8.5%), 4-trifluoromethylaniline ($^{19}$F-NMR yield: 7.2%) and 2,4-bis(trifluoromethyl)aniline ($^{19}$F-NMR yield: 4.2%). 2-trifluoromethylaniline 19F-NMR (deuterated dimethyl sulfoxide): δ−63.0.
MS (m/z): 161 [M]+
4-trifluoromethylaniline
19F-NMR (deuterated dimethyl sulfoxide): δ−61.3.
MS (m/z): 161 [M]+
2,4-bis(trifluoromethyl)aniline
19F-NMR (deuterated chloroform): δ−62.0, −63.7.
MS (m/z): 229[M]+.

Example 14

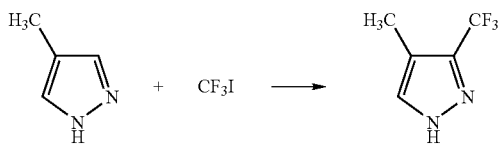

0.047 g (0.25 mmol) of ferrocene was weighed and placed in a two-neck flask and the atmosphere in the flask was replaced with argon. The following materials were added thereinto: 0.07 ml (0.88 mmol) of 4-methylpyrazole, 1.7 ml of dimethyl sulfoxide, 1.7 ml of a 1 N dimethyl sulfoxide solution of sulfuric acid, 0.7 ml of a 3.0 mol/l dimethyl sulfoxide solution of trifluoromethyl iodide and 0.15 ml of a 30% hydrogen peroxide aqueous solution, and the mixture was stirred for 20 minutes. During the stirring, the temperature of the reaction system rose up in the range of from 40° C. to 50° C. Thereafter the resulting solution was cooled to room temperature. Formation of 4-methyl-3-trifluoromethylpyrazole (19F-NMR yield: 45%) was confirmed by 19F-NMR with 2,2,2-trifluoroethanol as an internal standard. The subsequent procedure was conducted in the same manner as in Example 1 and 4-methyl-3-trifluoromethylpyrazole was obtained as a colorless oil (0.054 g, yield: 36%).

1H-NMR (deuterated dimethyl sulfoxide): δ2.12 (s, 3H), 7.73 (s, 1H), 13.29 (brs, 1H).
13C-NMR (deuterated dimethyl sulfoxide): δ7.62, 113.5, 122.5 (q, $J_{CF}$=268.7 Hz), 129.8, 138.7 (q, $J_{CF}$=34.2 Hz).
19F-NMR (deuterated dimethyl sulfoxide): δ−59.8.
MS (m/z): 150 [M]+.

Comparative Example 1

0.055 g (0.5 mmol) of uracil was weighed and placed in a two-neck flask and the atmosphere in the flask was replaced with argon. The following materials were added thereinto: 1.0 ml of a 1 N dimethyl sulfoxide solution of sulfuric acid, 0.5 ml of a 2.1 mol/l dimethyl sulfoxide solution of trifluoromethyl iodide and 0.15 ml of a 1.0 mol/l aqueous solution of iron(II) sulfate, and the mixture was stirred for 20 minutes. The subsequent procedure was conducted in the same manner as in Example 2. No formation of 5-trifluoromethyluracil was confirmed.

Comparative Example 2

0.055 g (0.5 mmol) of uracil was weighed and placed in a two-neck flask and the atmosphere in the flask was replaced with argon. The following materials were added thereinto: 1.0 ml of a 1 N dimethyl sulfoxide solution of sulfuric acid, 0.5 ml of a 2.1 mol/l dimethyl sulfoxide solution of trifluoromethyl iodide and 0.1 ml of a 30% hydrogen peroxide aqueous solution, and the mixture was stirred for 20 minutes. The subsequent procedure was conducted in the same manner as in Example 2. No formation of 5-trifluoromethyluracil was confirmed.

Comparative Example 3

0.055 g (0.5 mmol) of uracil was weighed and placed in a two-neck flask and the atmosphere in the flask was replaced with argon. The following materials were added thereinto: 1.0 ml of a 1 N acetone solution of sulfuric acid, 0.5 ml of a 2.1 mol/l acetone solution of trifluoromethyl iodide, 0.1 ml of a 30% hydrogen peroxide aqueous solution and 0.15 ml of a 1.0 mol/l aqueous solution of iron(II) sulfate, and the mixture was stirred for 20 minutes. The subsequent procedure was conducted in the same manner as in Example 2. No formation of 5-trifluoromethyluracil was confirmed.

INDUSTRIAL APPLICABILITY

The reaction reagent according to the present invention is industrially extremely useful as a versatile reagent enabling high-yield and efficient production of organic compounds with a trifluoromethyl group which are useful compounds for medical and agricultural chemicals, functional materials and manufacturing intermediates thereof.

The entire disclosure of Japanese Patent Application No. 2006-300571 filed on Nov. 6, 2006 including the specification, claims, and summary is incorporated herein by reference in its entirety.

The invention claimed is:

1. A reaction reagent for trifluoromethylation, which is used for introducing a trifluoromethyl group to a substrate, comprising an iron compound, trifluoromethyl iodide, a peroxide, a sulfoxide and an acid.

2. The reaction reagent for trifluoromethylation according to claim 1, wherein a molar ratio of the iron compound and trifluoromethyl iodide is in a range of from 1:1 moles to 1:100 moles.

3. The reaction reagent for trifluoromethylation according to claim 1, wherein a molar ratio of the iron compound and the peroxide is in a range of from 1:1 moles to 1:50 moles.

4. The reaction reagent for trifluoromethylation according to claim 1, wherein a molar ratio of the iron compound and the sulfoxide is in a range of from 1:50 moles to 1:30000 moles.

5. The reaction reagent for trifluoromethylation according to claim 1, wherein a molar ratio of the iron compound and the acid is in a range of from 1:0.001 moles to 1:50 moles.

6. The reaction reagent for trifluoromethylation according to claim 1, wherein the iron compound is iron(II) sulfate, ammonium iron(II) sulfate, iron(II) tetrafluoroborate, iron(II) chloride, iron(II) bromide, iron(II) iodide, iron(II) acetate, iron(II) oxalate, bis(acetylacetonato)iron(II), ferrocene, bis ($\eta^5$-pentamethylcyclopentadienyl)iron or an iron powder.

7. The reaction reagent for trifluoromethylation according to claim 1, wherein the iron compound is iron(II) sulfate, ammonium iron(II) sulfate, iron(II) tetrafluoroborate, ferrocene, bis($\eta^5$-pentamethylcyclopentadienyl)iron or an iron powder.

8. The reaction reagent for trifluoromethylation according to claim 1, wherein the peroxide is hydrogen peroxide, hydrogen peroxide-urea composite, tert-butyl peroxide or peroxyacetic acid.

9. The reaction reagent for trifluoromethylation according to claim 1, wherein the peroxide is hydrogen peroxide or hydrogen peroxide-urea composite.

10. The reaction reagent for trifluoromethylation according to claim 1, wherein the sulfoxide is dimethyl sulfoxide, dibutyl sulfoxide or diphenyl sulfoxide.

11. The reaction reagent for trifluoromethylation according to claim 1, wherein the sulfoxide is dimethyl sulfoxide.

12. The reaction reagent for trifluoromethylation according to claim 1, wherein the acid is sulfuric acid, hydrochloric acid, hydrobromic acid, hydroiodic acid, nitric acid, phosphoric acid, hexafluorophosphoric acid, tetrafluoroboric acid, formic acid, acetic acid, propionic acid, oxalic acid, p-toluenesulfonic acid, trifluoromethanesulfonic acid or trifluoroacetic acid.

13. The reaction reagent for trifluoromethylation according to claim 1, wherein the acid is sulfuric acid, tetrafluoroboric acid or trifluoromethanesulfonic acid.

* * * * *